US00PP19402P2

(12) United States Plant Patent
van der Knaap

(10) Patent No.: US PP19,402 P2
(45) Date of Patent: Nov. 4, 2008

(54) ***KALANCHOE* PLANT NAMED 'DON MARTINO'**

(50) Latin Name: *Kalanchoe blossfeldiana*
Varietal Denomination: Don Martino

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 0 days.

(21) Appl. No.: 11/974,212

(22) Filed: Oct. 11, 2007

(51) Int. Cl.
*A01H 5/00* (2006.01)

(52) U.S. Cl. ..... Plt./336
(58) Field of Classification Search ..... Plt./336
See application file for complete search history.

*Primary Examiner*—Annette H Para
(74) *Attorney, Agent, or Firm*—C. A. Whealy

(57) ABSTRACT

A new and distinct cultivar of *Kalanchoe* plant named 'Don Martino', characterized by its upright, uniform and vigorous growth habit; dark green-colored leaves; uniform and freely flowering habit; double white-colored flowers; and excellent postproduction longevity.

1 Drawing Sheet

Botanical designation: *Kalanchoe blossfeldiana.*
Cultivar denomination: 'Don Martino'.

BACKGROUND OF THE INVENTION

The present invention relates to a new and distinct cultivar of *Kalanchoe,* botanically known as *Kalanchoe blossfeldiana,* and hereinafter referred to by the name 'Don Martino'.

The new *Kalanchoe* is a product of a planned breeding program conducted by the Inventor in Naaldwijk, The Netherlands. The objective of the breeding program is to create new double-flowered *Kalanchoe* cultivars with attractive foliage and flower coloration.

The new *Kalanchoe* originated from a cross-pollination made by the Inventor in Naaldwijk, The Netherlands in January, 2005, of a proprietary selection of *Kalanchoe blossfeldiana* identified as code number 20040843-003, not patented, as the female, or seed parent with a proprietary selection of *Kalanchoe blossfeldiana* identified as code number 20010633-001, not patented, as the male, or pollen, parent. The cultivar Don Martino was discovered and selected by the Inventor as a flowering plant from within the progeny of the stated cross-pollination in a controlled environment in Naaldwijk, The Netherlands in December, 2005.

Asexual reproduction of the new *Kalanchoe* by vegetative terminal cuttings in a controlled environment in Naaldwijk, The Netherlands since 2006 has shown that the unique features of this new *Kalanchoe* are stable and reproduced true to type in successive generations.

SUMMARY OF THE INVENTION

The cultivar Don Martino has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Don Martino'. These characteristics in combination distinguish 'Don Martino' as a new and distinct cultivar of *Kalanchoe:*

1. Upright, uniform and vigorous growth habit.
2. Dark green-colored leaves.
3. Uniform and freely flowering habit.
4. Double white-colored flowers.
5. Excellent postproduction longevity.

Plants of the new *Kalanchoe* can be compared to plants of the female parent selection. Plants of the new *Kalanchoe* differ from plants of the female parent selection in the following characteristics:

1. Plants of the new *Kalanchoe* are larger than plants of the female parent selection.
2. Plants of the new *Kalanchoe* are more freely branching than plants of the female parent selection.
3. Plants of the new *Kalanchoe* and the female parent selection differ in flower color as plants of the female parent selection have white, pink and yellow tri-colored flowers.

Plants of the new *Kalanchoe* can also be compared to plants of the male parent selection. Plants of the new *Kalanchoe* differ from plants of the male parent selection in the following characteristics:

1. Plants of the new *Kalanchoe* are more compact than plants of the male parent selection.
2. Plants of the new *Kalanchoe* have smaller leaves than plants of the male parent selection.

Plants of the new *Kalanchoe* can be compared to plants of the *Kalanchoe blossfeldiana* cultivar Don Juan, disclosed in U.S. Plant Pat. No. 17,576. In side-by-side comparisons conducted in Naaldwijk, The Netherlands, plants of the new *Kalanchoe* differed from plants of the cultivar Don Juan in the following characteristics:

1. Plants of the new *Kalanchoe* were taller than plants of the cultivar Don Juan.
2. Flowers of plants of the new *Kalanchoe* had more petals than flowers of plants of the cultivar Don Juan.
3. Flowers of plants of the new *Kalanchoe* were longer-lasting than flowers of plants of the cultivar Don Juan.
4. Flowers of plants of the new *Kalanchoe* were white in color whereas flowers of plants of the cultivar Don Juan were red in color.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.*

The photograph at the top of the sheet comprises a side perspective view of a typical flowering plant of 'Don Martino' grown in a container.

The photograph at the bottom of the sheet comprises a top perspective view of a typical flowering plant of 'Don Martino'.

DETAILED BOTANICAL DESCRIPTION

The aforementioned photographs and following observations, measurements and values describe plants grown in Naaldwijk, The Netherlands in a glass-covered greenhouse during the summer and under conditions which closely approximate commercial production. During the production of the plants, day temperatures were about 20° C. to 25° C., night temperatures were about 18° C. to 22° C. and light levels ranged from about 5 kilolux to 60 kilolux. Plants grown in 12-cm containers received long day/short night conditions (more than 14 hours of light) for about four weeks; plants then received photoinductive short day/long night conditions (minimum 14 hours darkness) until flowering. Plants were about 14 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* cultivar Don Martino.

Parentage:

*Female, or seed, parent.*—Proprietary selection of *Kalanchoe blossfeldiana* identified as code number 20040843-003, not patented.

*Male, or pollen, parent.*—Proprietary selection of *Kalanchoe blossfeldiana* identified as code number 20010633-001, not patented.

Propagation:

*Type.*—By vegetative terminal cuttings.

*Time to initiate roots, summer.*—About ten days at temperatures of 21° C.

*Time to initiate roots, winter.*—About two weeks at temperatures of 21° C.

*Time to produce a rooted young plant, summer.*—About three weeks at temperatures of 21° C.

*Time to produce a rooted young plant, winter.*—About four weeks at temperatures of 21° C.

*Root description.*—Fine, fibrous; white in color.

*Rooting habit.*—Freely branching; dense.

Plant description:

*Plant habit.*—Upright, uniform and vigorous growth habit. Very freely flowering with numerous compound cymes. Inverted triangle with rounded crown. Appropriate for 10-cm to 13-cm containers.

*Plant height at flowering.*—About 20 cm.

*Plant diameter at flowering.*—About 30 cm.

Lateral branch description:

*Branching habit.*—Freely branching habit; usually about 14 lateral branches develop per plant.

*Length.*—About 10 cm to 16 cm.

*Diameter.*—About 1 cm.

*Internode length.*—About 1 cm.

*Aspect.*—Erect.

*Strength.*—Strong.

*Texture.*—Smooth, glabrous.

*Color.*—Close to 143A.

Foliage description:

*Arrangement.*—Opposite, simple; generally symmetrical.

*Length, generative plants.*—About 6 cm to 13 cm.

*Width, generative plants.*—About 3 cm to 9 cm.

*Shape.*—Ovate.

*Apex.*—Rounded.

*Base.*—Obtuse.

*Margin.*—Crenate; undulate.

*Texture, upper and lower surfaces.*—Glabrous, leathery; succulent.

*Venation pattern.*—Pinnate; reticulate.

*Color.*—Developing foliage, upper surface: Close to 137C. Developing foliage, lower surface: Lighter than 147B. Fully expanded foliage, upper surface: Close to 147A; venation, close to 146A. Fully expanded foliage, lower surface: Close to 147B; venation, 147B.

*Petiole.*—Length: About 0.5 cm to 2.5 cm. Diameter: About 5 mm to 8 mm. Texture, upper and lower surfaces: Smooth, glabrous. Color, upper surface: Close to 146A. Color, lower surface: Close to 144A.

Flower description:

*Flower arrangement and habit.*—Double flowers arranged singly in compound dichasial cymes that arise from leaf axils. Uniform and freely flowering habit with usually about twelve flowers developing per inflorescence. Flowers persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long conditions (at least 14 hours of darkness).

*Time to flower.*—Under short day/long night photoinductive conditions, about 70 days are required. Actual time to flower is primarily dependent upon temperature and light intensity.

*Post-production longevity.*—Excellent post-production longevity; flowers maintain good substance for about five weeks under interior environmental conditions.

*Inflorescence height.*—About 2 cm to 3 cm.

*Inflorescence diameter.*—About 1.5 cm to 4 cm.

*Flower diameter.*—About 1.8 cm.

*Flower length (height).*—About 1.3 cm.

*Flower bud.*—Shape: Ovoid to spherical. Length: About 5 mm to 8 mm. Diameter: About 2 mm to 4 mm. Color: Close to 2D.

*Petals.*—Arrangement: About 35 fused at the base. Length (largest petals): About 8 mm to 12 mm. Width (largest petals): About 4 mm to 5 mm. Aspect: Slightly upright to eventually recurved. Shape: Spatulate. Apex: Apiculate. Margin: Entire. Texture, upper and lower surfaces: Smooth, glabrous; satiny. Color: When opening, upper surface: Close to 155D; towards the base, close to 8C. When opening, lower surface: Close to 155D; towards the base, close to 10D. Fully opened, upper and lower surfaces: Close to 155D.

*Sepals.*—Appearance: Four fused at the base. Length: About 8 mm. Width: About 2 mm to 2.5 mm. Shape: Lanceolate. Apex: Acute. Margin: Entire. Texture, upper and lower surfaces: Smooth; glabrous. Color, upper and lower surfaces: Close to 144A.

*Peduncles.*—Length: About 9 cm. Diameter: About 3 mm to 5 mm. Aspect: Mostly erect. Strength: Strong. Texture: Smooth, glabrous. Color: Between 146B and 144A.

*Pedicels.*—Length: About 2 mm to 6 mm. Diameter: About 1 mm. Aspect: Erect to about 45° from vertical. Strength: Moderately strong. Texture: Smooth, glabrous. Color: Close to 146B.

*Reproductive organs.*—Androecium: Stamen number: About five per flower. Anther shape: Oval. Anther length: About 0.5 mm. Anther color: Close to 165B. Amount of pollen: None observed. Gynoecium: Pistil number: About four per flower. Pistil length: About 6 mm to 7 mm. Style length: About 1.5 mm. Style color: Close to 145C. Stigma shape: Rounded. Stigma color: Close to 154D. Ovary color: Close to 145B.

*Seed/fruit.*—Seed and fruit development have not been observed.

Temperature tolerance: Plants of the new *Kalanchoe* have been observed to tolerate temperatures from about 5° C. to about 35° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Don Martino' as illustrated and described.

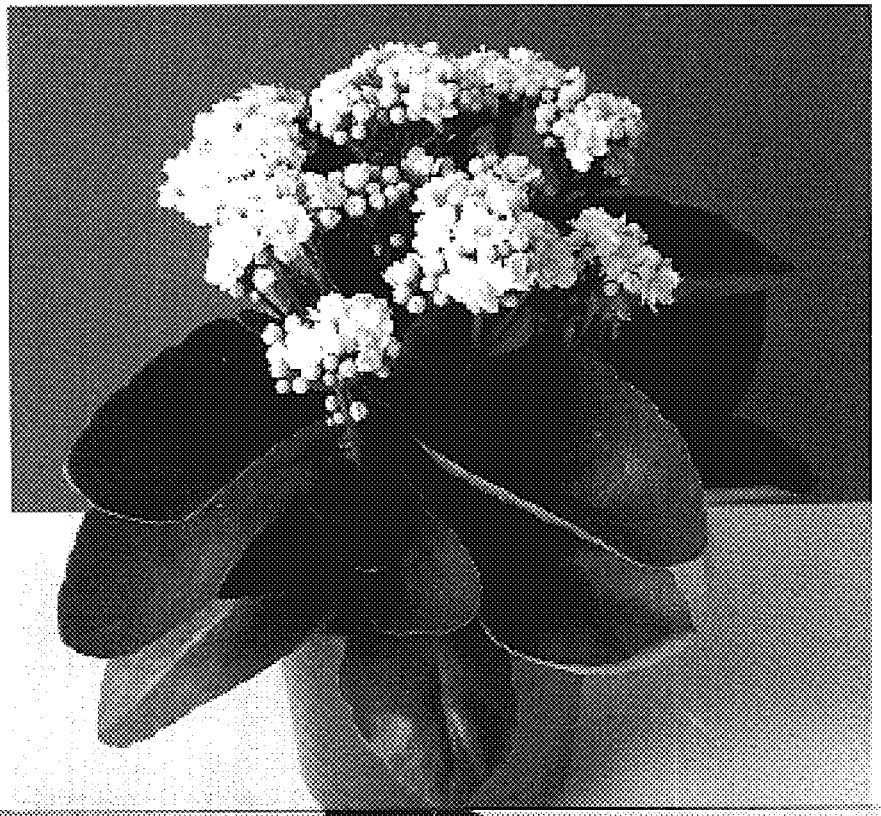
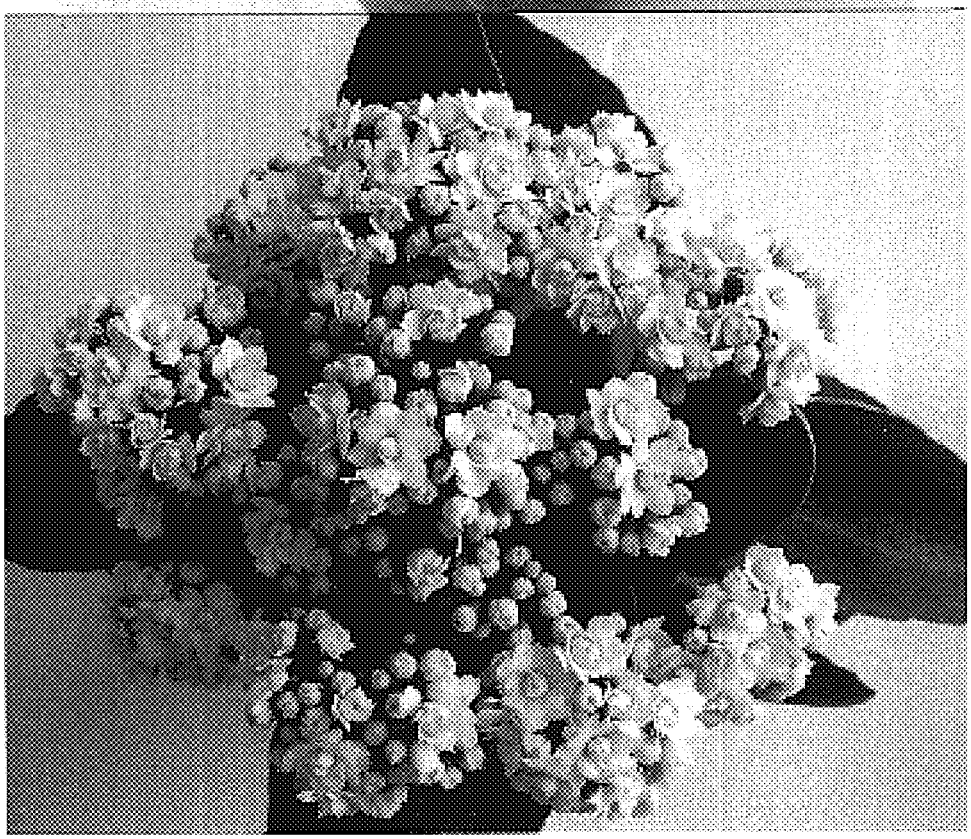

* * * * *